US007670280B2

(12) United States Patent

Gloth

(10) Patent No.: US 7,670,280 B2

(45) Date of Patent: *Mar. 2, 2010

(54) DEVICE AND METHOD FOR ENHANCING FEMALE SEXUAL STIMULATION

(76) Inventor: David Gloth, 16 Harcourt St., Apt. 61, Boston, MA (US) 02116

( * ) Notice: Subject to any disclaimer, the term of this patent is extended or adjusted under 35 U.S.C. 154(b) by 1390 days.

This patent is subject to a terminal disclaimer.

(21) Appl. No.: 11/008,332

(22) Filed: Dec. 9, 2004

(65) Prior Publication Data

US 2005/0256369 A1 Nov. 17, 2005

Related U.S. Application Data

(63) Continuation-in-part of application No. 10/842,957, filed on May 11, 2004, now Pat. No. 6,949,067.

(51) Int. Cl.
*A61F 5/00* (2006.01)

(52) U.S. Cl. .......................................................... 600/38

(58) Field of Classification Search ............. 600/38–41; 128/897, 898; 601/6, 12, 78–81; 607/1, 607/96, 108, 114

See application file for complete search history.

(56) References Cited

U.S. PATENT DOCUMENTS

| | | | | |
|---|---|---|---|---|
| 2,120,367 | A | 6/1938 | Lewis | |
| 2,212,706 | A | 8/1940 | Cohn et al. | |
| 2,711,172 | A | 6/1955 | Booth | |
| 2,792,003 | A | 5/1957 | Cantor | |
| 3,820,533 | A * | 6/1974 | Jones | 600/38 |
| 4,224,933 | A | 9/1980 | Reiling | |
| D320,084 | S | 9/1991 | Stewart et al. | |
| 5,067,480 | A | 11/1991 | Woog et al. | |
| 5,103,810 | A | 4/1992 | Chang | |
| 5,333,621 | A | 8/1994 | Denzer | |
| 5,690,603 | A | 11/1997 | Kain | |
| 5,725,473 | A | 3/1998 | Taylor | |
| 5,755,236 | A | 5/1998 | Dann et al. | |
| 5,813,973 | A | 9/1998 | Gloth | |
| 5,853,362 | A | 12/1998 | Jacobs | |
| 5,877,216 | A | 3/1999 | Place et al. | |
| 5,885,233 | A | 3/1999 | Adachi | |
| 5,895,349 | A | 4/1999 | Tihon | |
| 5,920,923 | A | 7/1999 | Jillette | |

(Continued)

FOREIGN PATENT DOCUMENTS

EP 289587 A1 11/1988

(Continued)

OTHER PUBLICATIONS

Vibrating Clit Massager, Adam & Eve catalog, Nov. 2001, 2 pages.*

(Continued)

*Primary Examiner*—Samuel G Gilbert

(57) ABSTRACT

A female stimulation device and method for enhancing female sexual stimulation. The device includes a body having a tip portion, a flange, and an intermediate side wall portion. The intermediate side wall portion extending from the tip portion to the flange. The vacuum produced by the device can be controlled, and additional structures and elements may be added to enhance clitoral blood flow and stimulation without causing injury when the device is applied to a user.

28 Claims, 5 Drawing Sheets

U.S. PATENT DOCUMENTS

| | | | |
|---|---|---|---|
| 5,989,180 A | 11/1999 | Norton et al. | |
| 5,997,469 A | 12/1999 | Northcutt | |
| 6,056,705 A | 5/2000 | Stigar-Brown | |
| 6,067,663 A | 5/2000 | Fernandez | |
| 6,099,463 A * | 8/2000 | Hockhalter | 600/38 |
| 6,132,366 A | 10/2000 | Ritchie et al. | |
| 6,179,774 B1 | 1/2001 | Landry | |
| 6,179,775 B1 | 1/2001 | Thompson | |
| D443,057 S | 5/2001 | Hovland et al. | |
| 6,224,541 B1 | 5/2001 | Thompson | |
| 6,246,915 B1 | 6/2001 | Boutos | |
| 6,250,304 B1 | 6/2001 | Turner | |
| 6,294,550 B1 | 9/2001 | Place et al. | |
| D449,690 S | 10/2001 | Hovland et al. | |
| 6,306,841 B1 | 10/2001 | Place et al. | |
| 6,322,493 B1 | 11/2001 | Thompson | |
| 6,464,653 B1 | 10/2002 | Hovland et al. | |
| 6,469,016 B1 | 10/2002 | Place et al. | |
| 6,537,260 B1 | 3/2003 | Lamb et al. | |
| 6,578,205 B1 | 6/2003 | King | |
| 6,593,313 B2 | 7/2003 | Place et al. | |
| 6,702,733 B1 | 3/2004 | Thompson | |
| 6,733,438 B1 | 5/2004 | Dann et al. | |
| 6,737,084 B2 * | 5/2004 | Crosby et al. | 424/725 |
| 6,749,557 B2 | 6/2004 | Garland | |
| D494,676 S | 8/2004 | Dubniczki et al. | |
| 6,923,755 B2 | 8/2005 | Norma | |
| 6,935,343 B1 | 8/2005 | Turner | |
| 2001/0051656 A1 | 12/2001 | Place et al. | |
| 2002/0013289 A1 | 1/2002 | Pendergast et al. | |
| 2002/0165429 A1 | 11/2002 | Thompson | |
| 2002/0177582 A1 | 11/2002 | Maloney | |
| 2003/0023139 A1 * | 1/2003 | Hartz | 600/38 |
| 2003/0170325 A1 | 9/2003 | Mermelstein et al. | |
| 2003/0171647 A1 | 9/2003 | Garland | |
| 2003/0207852 A1 | 11/2003 | Place et al. | |
| 2004/0044328 A1 | 3/2004 | Kemp et al. | |
| 2004/0059190 A1 | 3/2004 | Matlock | |
| 2004/0186344 A1 | 9/2004 | Jannuzzi | |
| 2004/0230093 A1 | 11/2004 | Marshall et al. | |
| 2004/0260252 A1 | 12/2004 | Dipiano et al. | |
| 2005/0124853 A1 | 6/2005 | Norma | |
| 2005/0165367 A1 | 7/2005 | Higgins | |
| 2006/0047182 A1 | 3/2006 | Cochran | |

FOREIGN PATENT DOCUMENTS

| | | |
|---|---|---|
| EP | 861067 | 9/1998 |
| JP | 3212793 | 7/2003 |
| WO | WO 97/28766 A1 | 8/1997 |
| WO | WO 99/21562 | 5/1999 |
| WO | WO 00/28939 A2 | 5/2000 |
| WO | WO 2004/058134 A2 | 7/2004 |
| WO | WO 2004/064913 A1 | 8/2004 |
| WO | WO 2005/072319 A2 | 8/2005 |

OTHER PUBLICATIONS

Juicy Lucy, The Xandria Collection, Oct. 20, 2000, 2 pages.*

"FDA Clears New Sexual Therapy Device," Medical Letter on the CDC & FDA, May 20, 2000, Charles W. Henderson, Atlanta, GA.

Laviolette and Meunier, "Vaginal Dryness," Quebec Pharmacie (Canada), Nov.-Dec. 2004, vol. 51 (Abstract).

PCT International Search Report mailed Aug. 24, 2005 (citing references 5,813,973, 5,895,349, WO97/28766, 5,755,236, 5,989,180, WO00/28939, 6,224,541, WO2004/058134 and 6,733438).

* cited by examiner

DEVICE AND METHOD FOR ENHANCING FEMALE SEXUAL STIMULATION

RELATED APPLICATIONS

This application claims the benefit under 35 U.S.C. § 120 of U.S. patent application Ser. No. 10/842,957, entitled "A DEVICE AND METHOD FOR ENHANCING FEMALE SEXUAL STIMULATION," filed on May 11, 2004, which is herein incorporated by reference in its entirety.

BACKGROUND OF INVENTION

1. Field of Invention

The present invention relates generally to a device and method to increase female sexual stimulation and, more specifically, to a female stimulation device and method which provides vascular engorgement and stimulation.

2. Description of the Related Art

Clitoral vascular engorgement plays an important role in female sexual arousal and satisfaction. Sexual arousal results in smooth muscle relaxation and arterial vasodilation within the clitoris. The resultant increase in blood flow leads to tumescence of the glans clitoris and increased sexual arousal. A variety of diseases, such as arteriosclerosis and diabetes, may cause clitoral erectile insufficiency and reduced clitoral arterial flow. This, in turn, may lead to difficulty or inability to achieve clitoral tumescence, especially in women who suffer from female sexual arousal disorder (FSAD). FSAD may be expressed as a lack of either subjective excitement, genital lubrication or orgasmic function.

The most effective method of increasing clitoral engorgement, especially in women suffering from FSAD, is through use of suction. A partial vacuum placed over the clitoris creates negative pressure in the organ which promotes clitoral arterial inflow and venous congestion and results in increased vascular engorgement and sexual arousal. One device for stimulating female sexual response that is designed to be applied in the clitoral region is described in U.S. Pat. No. 6,733,438, which is incorporated herein by reference in its entirety. It consists of a vacuum-producing, partially deformable device of unitary construction having a distal tip portion, a flange and intermediate side walls which, when placed over the clitoris of the user, stimulates blood flow and sexual response. The intermediate side walls are outwardly convex so as to retain its shape rather than collapse when vacuum is applied. The side walls may be reinforced with internal or external arches. The arched geometry prevents side wall collapse and clitoral compression with injury.

SUMMARY OF INVENTION

In accordance with one or more embodiments, the present invention can provide a female stimulation device. The device includes a body having a tip portion, a flange, and an intermediate side wall portion. The intermediate side wall portion extending from the tip portion to the flange. The device also includes means for enhancing clitoral blood flow when applied to a user.

In accordance with one or more embodiments, the present invention can also provide a method for facilitating female stimulation. The method includes providing a device comprising a tip portion, a flange, an intermediate side wall portion extending outwardly from the tip portion to the flange, and means for enhancing clitoral blood flow when applied to a user. The flange is sized and shaped to encompass the female clitoris. The intermediate side wall portion is outwardly convex and defines a vacuum reservoir lower chamber. The tip portion is deformable and defines a vacuum producing upper chamber, and the means for enhancing clitoral blood flow comprises at least one of a mechanical, vibratory, or heating component. The method further includes providing instruction to apply the device to promote clitoral blood flow without causing injury to underlying tissue.

In accordance with one or more embodiments, the present invention can also provide a method for enhancing female stimulation. The method includes providing a female stimulation device comprising a tip portion, a flange, an intermediate side wall portion extending from the tip portion to the flange and defining an interior vacuum chamber, and means for enhancing clitoral blood flow when applied to a user. The tip portion is compressed to reduce an air column formed within the interior vacuum chamber. The device is placed over the female clitoris such that the flange is placed into contact with, and the means for enhancing clitoral blood flow is, in operative contact with the anterior vaginal vault tissue. The tip portion is released to produce vacuum in the interior vacuum chamber. The vacuum causes clitoral engorgement and maintains engagement of the device with the anterior vaginal vault tissue. The device may be removed after a predetermined period of time. The method may be repeated periodically to condition and treat genital tissues.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
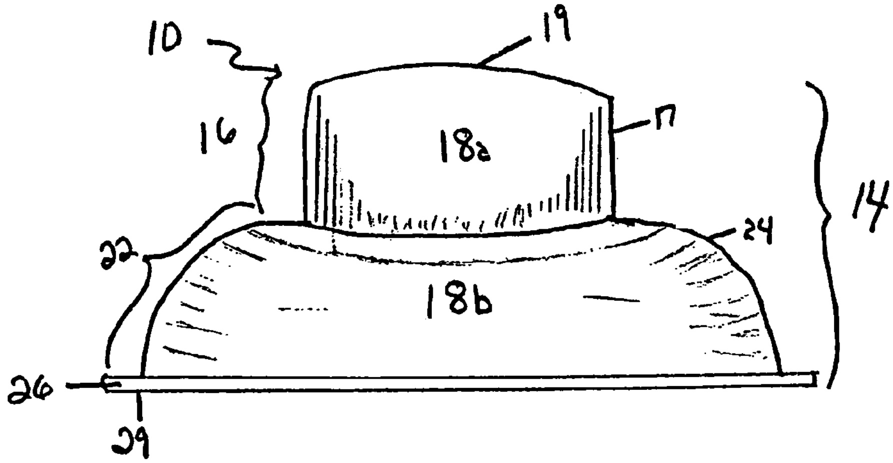
FIG. 1 is a perspective view of a female stimulation device in accordance with the invention.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

In accordance with the present invention, a device for stimulating the clitoris of a female includes a resilient and at least partially deformable device body having an enclosed tip portion, a flange and an outwardly convex, intermediate side wall portion. In use, the device body is placed over the clitoris of the user and the tip portion is deformed, causing a vacuum environment to be formed in an interior chamber formed by the device body. The device provides suction to the clitoris, thereby stimulating vascular engorgement and sexual arousal. A biocompatible lubricant, adhesive, or pharmacologically active material such as vasoactive agent, may be applied to the flange in order to enhance the vacuum seal and to further increase clitoral blood flow. The amount of lubricant or pharmacologically active material should be on the order of 3 mm thickness or less to avoid device slippage.

For women with FSAD, stimulation of the clitoris by suction can be aided by mechanical manipulation, vibratory motion, and/or heat. Therefore, the device for stimulating the clitoris of a female may further include additional structures and elements to increase or enhance clitoral blood flow and stimulation. Such structures may include mechanical attachments secured to the device to contact the clitoral tissue without compressing, obstructing or pinching. Another embodiment may include vibratory devices secured to a portion of device body, and electronically or mechanically operated to enhance clitoral blood flow. Another embodiment may include the use of a heat-producing compound on or in a surface-contacting portion of the device to stimulate the user. All of these supplemental structures may be used in combination with the vacuum producing device to increase the overall efficiency of the device and enhance stimulation of the user.

As noted, in addition to the vacuum portion, the device may also include mechanical attachments, such as a plurality of thin, flexible, soft attachments, secured to an interior aspect of the intermediate side wall or tip portion and dangling into the lower vacuum chamber housing the clitoris (after the device is applied by the user). After the device is applied, movement by the user would cause motion of these attachments, thereby creating additional clitoral stimulation by mechanical manipulation. In an alternative embodiment, the device may include a plurality of roller elements, which may have a spherical shape, contained within a channel placed around the device. Movement by the user would cause the elements to collide, thereby creating additional clitoral stimulation by vibratory effects. In yet another alternative embodiment, the device may include a vibrator motor. After the device is applied by the user, the motor can be engaged, thereby creating additional clitoral stimulation by vibratory effects.

According to a further aspect of the invention, the inside of the device may be heated to provide increased warmth and vasodilation to the genital area. This heated effect can be accomplished by directly heating the device before application or by applying heat-generating compounds onto the flange or within the interior chamber of the device. The combination of heat and vacuum synergistically increase blood flow to the clitoris.

A method for increasing female sexual stimulation includes placing on the clitoris of the outer a device body having a tip portion, a flange and an outwardly convex, intermediate side wall so that the device body encompasses the clitoris. Deforming the tip portion will create a vacuum within the interior chamber, thereby stimulating vascular engorgement and sexual arousal. The method further includes additional clitoral stimulation by at least one of mechanical manipulation by a plurality of mechanical attachments extending into the lower vacuum chamber; vibratory motion produced mechanically or electronically; or heating of tissue by compounds applied to the flange or inner surface of the interior chamber of the device.

With the arrangement of the device of the present invention, a small, simple, and effective female clitoral stimulation device provides suction and enhanced stimulation to the clitoris, thereby stimulating vascular engorgement and sexual arousal. Advantageously, the device does not require an external vacuum source or associated tubing or connections. The device is simple to use, permitting the user to perform her daily activities while wearing it in an undetectable and discreet fashion.

In some embodiments the intermediate side wall portion has an outwardly convex shape. With this geometry, the intermediate side wall portion is substantially non-deformable in response to deformation of the tip portion. The vacuum producing tip portion is deformable while the outwardly convex geometry of the intermediate side wall permits the lower chamber to retain its shape, serving as a soft, yet functionally non-deformable, vacuum reservoir. With this arrangement, the device may be of unitary construction, manufactured from a single, soft, deformable material, yet possess both deformable and non-deformable portions. Furthermore, the soft, deformable material comprising the functionally non-deformable lower chamber will form a substantially fixed volume lower vacuum chamber over the clitoris, thereby preventing side wall abutment with associated tissue compression to genital tissue. The soft flange will prevent pressure necrosis of genital tissue when compared to rigid, non-deformable materials.

In some embodiments, the device may be made disposable by constructing it from low-tear strength materials. The low-tear strength materials permit the device to easily tear apart after one or more applications. To further increase the disposability of the low-tear strength material, one or more slits can be made in the flange. In another embodiment, the device can be made disposable by including a biodegradable plug in the tip portion which would degrade upon contact with the moist vaginal tissue. Once dissolved, an open channel would connect the device's inner vacuum chamber to the outside, therefore destroying the vacuum-producing potential for the device. In another embodiment, a patch of material can be attached over a hole in the wall of the device. Upon multiple uses, the patch will tear away. In another embodiment, a portion of a wall of the device is constructed extremely thin so as to rupture upon multiple uses. Disposability enhances safety by avoiding infection or contamination.

In some embodiments a method for increasing female sexual stimulation includes placing on the clitoris of the user a device body having a tip portion, a flange and an intermediate side wall portion extending outwardly from the tip portion to the flange so that the device body encompasses the clitoris. The method further includes deforming the tip portion so as to create a vacuum chamber within the device body. The intermediate side wall portion is substantially non-deformable in response to deformation of the tip portion. In the preferred embodiment, this is achieved by providing the intermediate side wall portions with an outwardly convex shape. With this arrangement, a fixed volume lower vacuum chamber is formed over the clitoris of the user in a simple manner that prevents pinching or compression of the clitoris. Furthermore, with this arrangement, the device may be of unitary construction, manufactured from a single, soft, compressible material, yet possess both deformable and non-deformable portions. The soft, yet functionally non-deformable, lower chamber and flange will further minimize tissue injury from compression or pressure necrosis.

Referring now to FIG. 1, a female stimulation device 10 includes a device body 14 having a tip portion 16 distal from the user's body, a flange 26 and a substantially non-deformable intermediate side wall portion 22 extending outwardly from the tip portion to the flange. The device body 14 defines an interior vacuum chamber composed of two sub-chambers; a deformable vacuum-producing upper chamber 18*a* and a non-deformable vacuum 30 reservoir lower chamber 18*b*. The flange 26 includes body-contacting surface 29.

The tip portion 16 has a substantially circular shape with vertical side walls 17 and a curved or flat end wall 19 which serves as a gripping portion to facilitate application and removal of the device. The interior of the tip portion 16 defines the upper chamber 18*a*. The tip portion is at least partially deformable or compressible in order to produce a partial vacuum within the interior vacuum chamber sufficient to seal the device 10 to the user's body by the differential in air pressure between the air within the vacuum chamber and the atmospheric air pressure.

The intermediate side wall portion 22 extends outwardly from the bottom of the tip portion 16 to the flange 26. The interior of the intermediate side wall portion 22 forms a lower vacuum chamber 18*b*. The intermediate side wall portion 22 is designed to be substantially non-deformable and maintain its shape when vacuum is applied so as to avoid compression of the clitoris. In the illustrated embodiment the intermediate side wall portion 22 is outwardly convex. With this arrangement, the intermediate side walls 24 are prevented from folding inward and abutting when vacuum is applied. This, in turn, prevents pinching or compression of the clitoris which is positioned within the lower vacuum chamber 18*b*.

The body-contacting surface 29 of the flange 26 forms a continuous seal around the clitoris of the user. The seal may be enhanced with the use of an adhesive material or non-adhesive lubricant such as water-based gels, petroleum-based gels or hydrophilic, water-soluble polymers disposed on the body-contacting surface 29 of the flange 26. In another embodiment the body-contacting surface 29 may be coated with a pharmacologically active material that enhances clitoral blood flow, vaginal lubrication and vaginal sensation including 1) vasoactive agents such as prostaglandins, endothelial-derived relaxation factors, vasoactive interstitial polypeptide agonists, smooth muscle relaxants, leukotriene inhibitors, L-arginine and others, and 2) medications and substances that increase clitoral stimulation such as estrogens, methyltestosterone and apomorphine. The amount of material should be less than about 3 mm thickness on surface 29 to avoid device slippage.

Typically, device 10 is constructed of any resilient material that is at least partially deformable. The material should be suitable for application to the human body in the manner described. Such materials include silicone, thermoplastic elastomers, urethanes, or rubber materials. One particularly effective material for use in constructing device 10 has been found to be silicone rubber. Preferably, 30-60-durometer silicone rubber is effective. Most preferably, 40-durometer silicone rubber has been shown to be effective. It will be appreciated that although intermediate side walls 24 are comprised of a resilient, deformable material, the side walls are made substantially non-deformable in response to deformation of tip portion 16 by their geometry, which is outwardly convex in one embodiment. With this arrangement, the device may be of unitary construction and manufactured from a single, soft, deformable material, yet possess both deformable and non-deformable portions. In other words, the lower chamber may be formed from a soft material, yet be functionally non-deformable when vacuum is applied. Furthermore, the resilient, deformable material is generally soft in contacting area tissue. Therefore, the lower chamber and flange will minimize pressure necrosis and any potential damage to genital tissue when compared to rigid, non-deformable materials. As will be further appreciated, other manners of rendering the side walls substantially non-deformable in response to deformation of the tip portion are possible including, but not limited to, material selection, geometry, dimensions and reinforcing features.

In general, device dimensions are dictated by the typical female anatomy so as to comfortably fit over the clitoris within the anterior vaginal vestibule. In the preferred embodiment, the outer radii extending from the center of device 10 to the ends of intermediate side wall portion 22 may vary between about 0.50 cm and about 1.75 cm. The radii of tip portion 16 will vary in proportion to the dimensions stated above, but generally will be between about 0.25 cm and about 0.75 cm, respectively. Preferably, body-contacting surface 29 of flange 26 contacts vaginal tissue adjacent to the outer perimeter of the clitoris. With this arrangement, the efficacy of the device is enhanced by providing a focused vacuum area. The height of device 10 can also vary, but should comfortably fit within the anterior vaginal vestibule without excessive protrusion while also being capable of being accessible for handling. In the preferred embodiment, the height of device 10 is between about 1.5 cm and about 3.0 cm; more preferably, the height of device 10 is between about 2.0 cm and about 2.5 cm; most preferably, the height of device 10 is approximately 2.0 cm. It will be appreciated, however, that the exact dimensions and shape of device 10 can vary without departing from the spirit of the invention.

The vacuum by the device can be controlled by the user. The amount of compression of tip portion 16 of device 10 regulates the amount of negative pressure within internal vacuum chamber 18. If the user compresses tip portion 16 more vigorously, the negative pressure or vacuum increases. In the preferred embodiment, as clinical studies have demonstrated, negative pressures should enhance clitoral blood flow without causing clitoral injury. The studies have demonstrated that to achieve enhanced clitoral blood flow without causing clitoral injury, device 10 should produce a range of negative pressure between about 40 and about 190 mmHg. If negative pressures exceed about 190 mmHg, excessive suction may place users at risk and may result in bleeding, discomfort and tissue injury. Alternatively, negative pressures below about 40 mmHg will result in inadequate stimulation of blood flow to the clitoris, or in failure of the device to self-adhere to the genital area. Device 10, therefore, can be calibrated for its size, shape, and materials of construction to allow for a range of vacuum pressure of between about 40 mmHg and about 190 mmHg.

In use, the device 10 is applied over the clitoris of the user. The vacuum produced in the lower vacuum chamber 18*b* causes increased clitoral blood flow and tumescence and improved sexual satisfaction. However, stimulation of the clitoris can be improved even further by combining clitoral suction with other methods of clitoral stimulation, including mechanical manipulation, genital heating, and/or vibratory motion. The structures described below to provide enhanced (or improved) stimulation may be used separately or in combination with the suction effects of the device. In addition, it is noted that alternative structures may be incorporated onto the device to provide additional stimulus for the wearer.

Figure 2A:
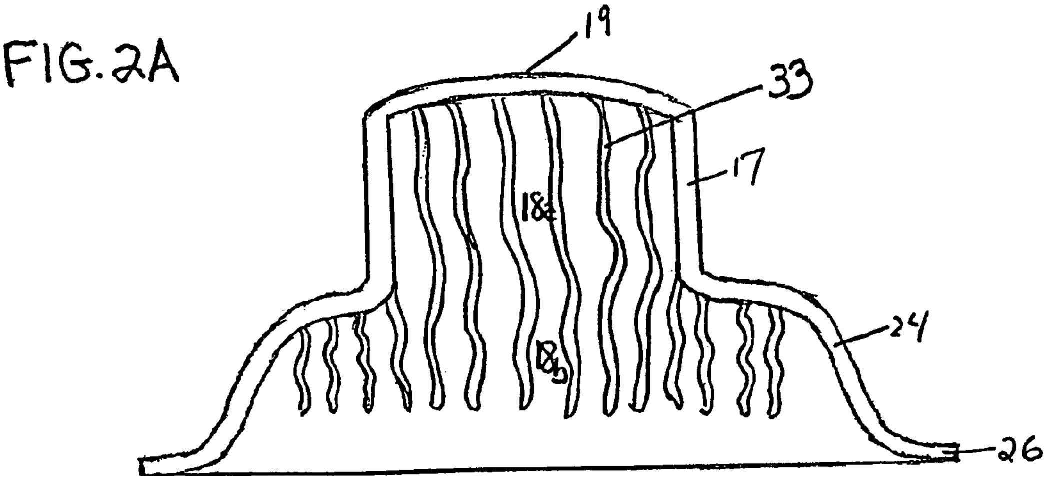
FIG. 2A is a cross-sectional side view of the device of FIG. 1, in which a plurality of flexible attachments that extend into the vacuum reservoir lower chamber.
Figure 2B:
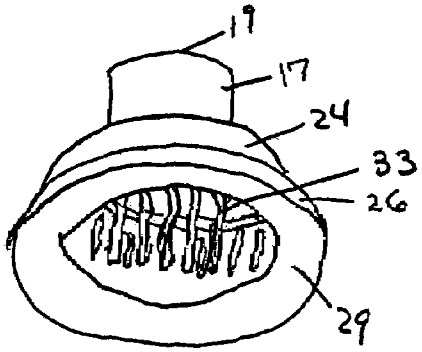
FIG. 2B is a bottom perspective view of the device of FIG. 2A.

Referring now to FIGS. 2A and 2B, a plurality of mechanical attachments, which may be in any variety of sizes and shapes provided they are soft and flexible in contact with the clitoris. In FIGS. 2A and 2B, the mechanical attachments are illustrated as thin, soft, flexible attachments 33. Attachments 33 are secured to and hang from the interior walls of the intermediate side wall portion 24 and/or the end wall 19 of the tip portion 16 and extend into the non-deformable lower chamber 18*b* to contact the user. Attachments 33 may be made of a material that is compatible with the device body (the same or different material), and may be molded as part of the device or secured separately. As the user moves about with the device in place, such motion will cause the attachments 33 to sway back and forth within the lower chamber 18 and gently stroke the clitoris. This stroking action will provide sufficient manual friction to further increase sexual excitement above that provided by the vacuum alone.

Figure 3A:
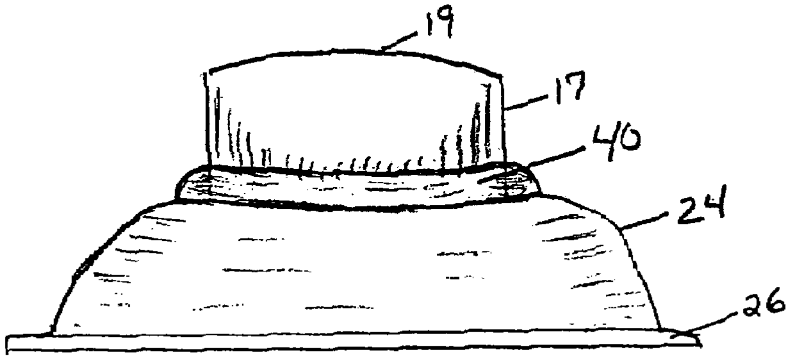
FIG. 3A is a perspective view of another embodiment of the invention.
Figure 3B:
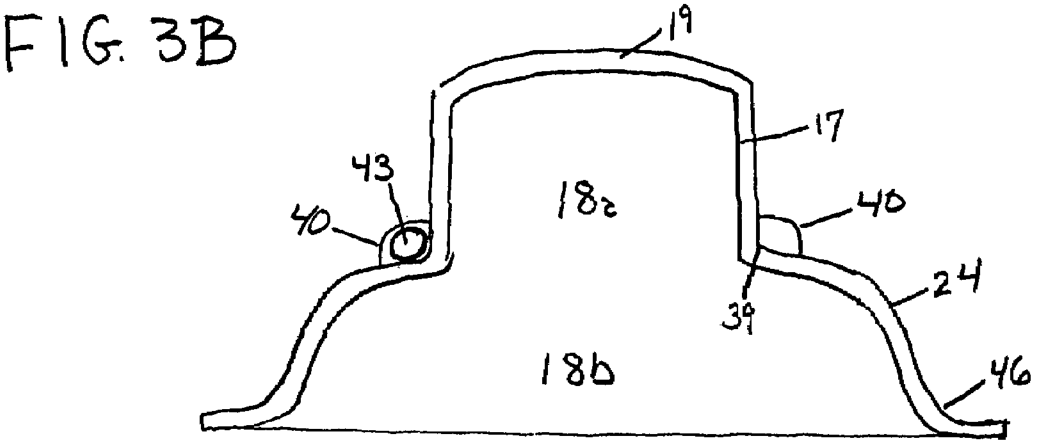
FIG. 3B is a cross-sectional side view of the device of FIG. 3A in which roller elements are positioned within a channel positioned between the tip portion and the intermediate side wall portion.

In a further embodiment shown in FIGS. 3A and 3B, a roller element 43 can travel within a hollow channel 40 that is positioned on device 10. Channel 40 is positioned at an appropriate position to allow the vibration caused by movement of the roller element to travel to the clitoris of the wearer. In the illustrated embodiment shown in FIG. 3A and 3B, channel 40 is positioned at the junction 39 of tip portion 16 and intermediate side wall 24. Alternatively, the channel may be positioned at or near the junction 46 of intermediate side wall 24 and flange 26. Channel 40 may be formed as part of the device body of a similar material; alternatively, the channel may be made of any other compatible material and secured separately to the device. At least one roller element, shown in the form of a spherical element 43, may move freely within hollow channel 40. As the user moves about with the device in place, such motion will cause the small spheres to roll within the hollow channel 40 and strike each other, thereby creating a vibratory effect within the device. This vibratory effect will be transmitted to the underlying clitoris and provide increased sexual excitement. Although shown as a spherical element, it should be appreciated that roller element 43 can be in any shape that would allow it to move within the channel 40 and provide an adequate vibratory response to movement by the wearer of the device to enhance clitoral stimulation.

Figure 4A:
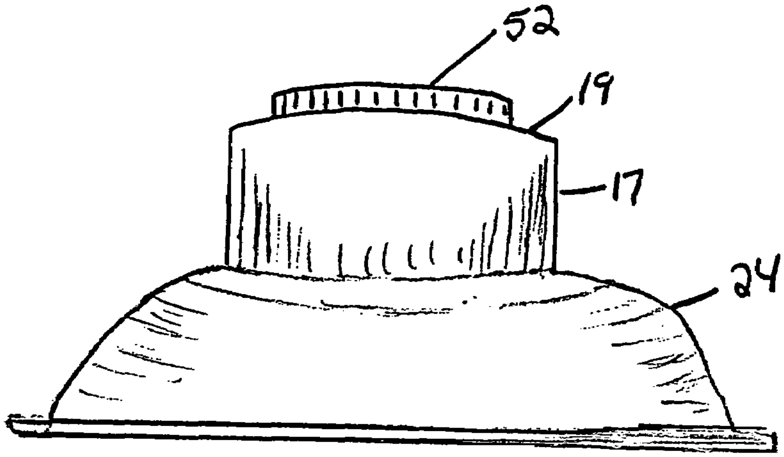
FIG. 4A is a perspective view of another embodiment of the invention in which a motor is attached to the tip portion.
Figure 4B:
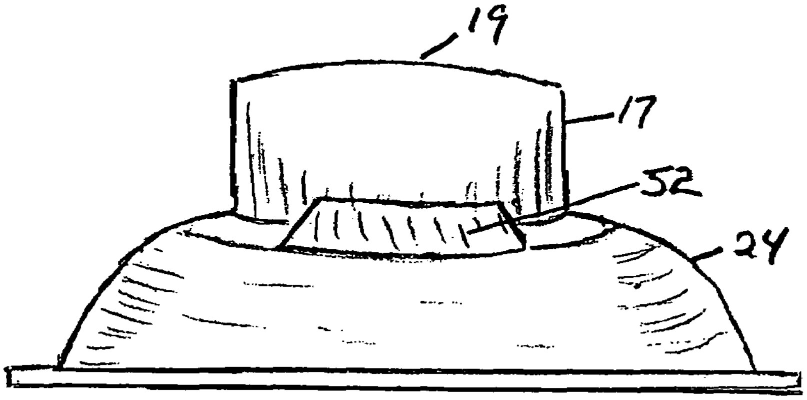
FIG. 4B is a perspective view of another embodiment of the invention in which a motor is attached to the intermediate side wall portion.

In a further embodiment shown in FIGS. 4A and 4B, a mechanical vibratory motor 52 may be attached to either end wall 19 of tip portion 16 or to the intermediate side wall portion 22. The vibratory motor may be activated manually or by remote control once the device 10 is positioned and secured by the user. The vibratory movement caused by the motor will be transmitted to the underlying clitoris and provide increased sexual excitement. The combination of the vibratory motion with vacuum will enhance the efficacy of the device. Motor element 52 can be secured to the device in any of a variety of ways, all well known to those skilled in the art. For example, motor may be secured to device 10 by suitable adhesive. Likewise, it is appreciated that the arrangement and operation of motor 52 are well known to those skilled in the art.

Figure 5:
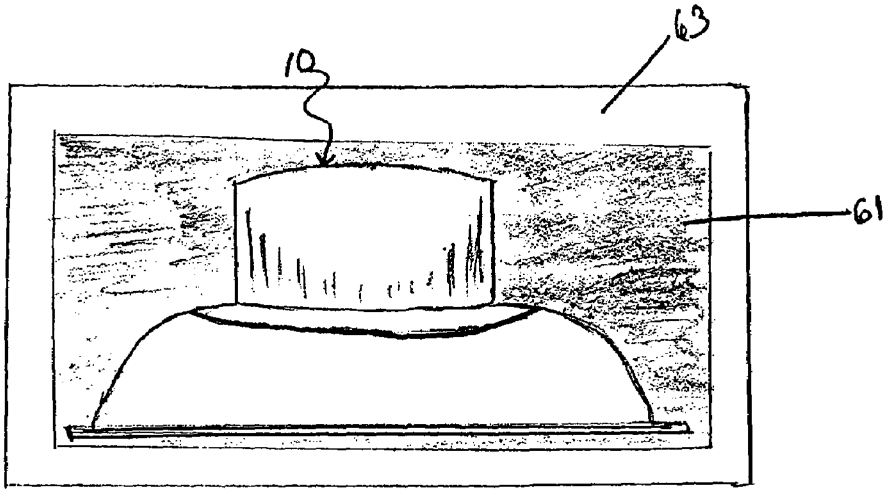
FIG. 5 is a perspective view of a female stimulation device according to a further embodiment of the invention in which the device is surrounded by a heat-producing compound.
Figure 6A:
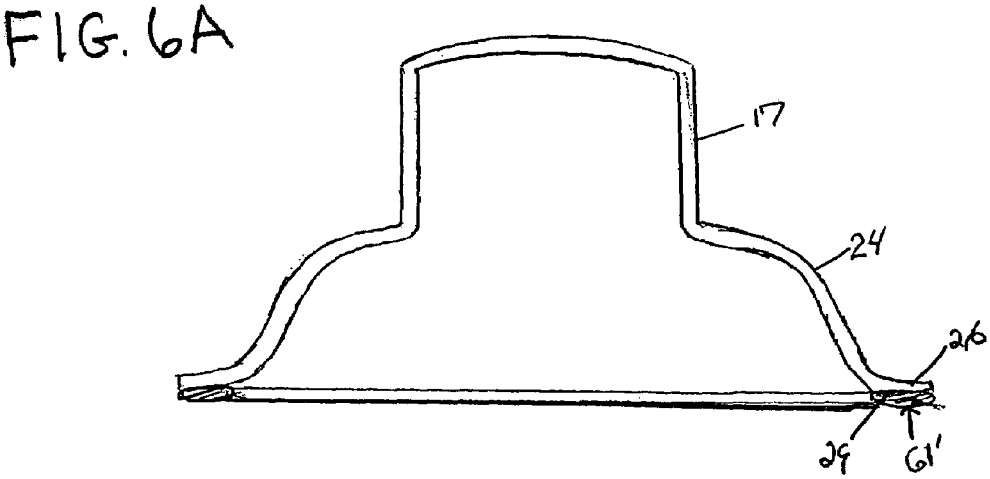
FIG. 6A is a cross-sectional side view of another embodiment of the invention in which the heat-producing compound is applied to the flange.
Figure 6B:
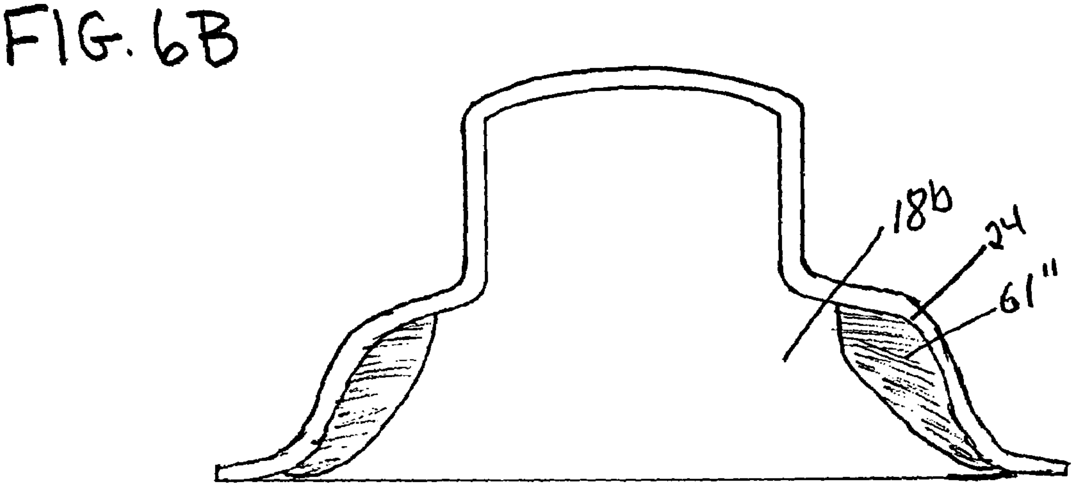
FIG. 6B is a cross-sectional side view of another embodiment of the invention in which the heat-producing compound is applied to the inner surface of the intermediate side wall.

In further embodiment shown in FIGS. 5, 6A and 6B, thermal energy may be used to warm the device and surrounding genital tissues (upon application of the device). Local application of heat to tissue will result in vasodilation and increased blood flow. Thermal energy may be applied by a variety of mechanisms. Referring to FIG. 5, in one embodiment, the device can be packaged so that it is surrounded by a thermal pack 61, which contains a heat-generating compound surrounded by a non-permeable membrane barrier. Heat-generating compounds for topical applications are well known and commercially available. When package 63 is opened, the user can activate thermal pack 61. Within a short time the thermal pack 61 heats to a temperature slightly in excess of body temperature, thereby also heating the enclosed device. After sufficient heating, the user applies the pre-warmed device over the clitoris. Referring to an alternative embodiment in FIG. 6A, thermal pack 61' is fashioned to fit the body-contacting surface of the flange 29. The thermal pack 61' consists of a heat-generating compound surrounded by a non-permeable membrane barrier and is securely attached to the body-contacting surface of the flange 29. The thermal pack 61' may cover either the entire or only part of the body-contacting surface of the flange 29. The user can activate the thermal pack, permit it to warm to an appropriate temperature, apply a lubricant to the exposed non-permeable membrane, and place the device, with the thermal pack conventionally attached thereto, to the genital area. Tissue warming occurs from the direct contact of the attached thermal pack 61' to the underlying genital tissue. The thermal pack 61' also functions as a soft pad on the body-contacting surface of the flange 29, thereby enhancing device comfort and fit.

The heat-producing material is most typically encapsulated non-permeable membrane barrier and activated to produce a reaction that generates heat. In this embodiment the heat-producing material is not in direct contact with the genital tissue of the user. In another embodiment, commercially available warming lubricants can be used to provide both warming and lubrication with the device. Such warming lubricants can be applied either to the device or directly to the tissue prior to application of the device in the manner described below.

Referring to another alternative embodiment in FIG. 6B, thermal pack 61" is fashioned to fit within the lower vacuum chamber 18*b* and is securely attached to the inner wall of the intermediate side wall portion 24 of the device. The thermal pack 61" may cover either the entire or only part of the inner wall surface. As in the previous embodiment, the user activates the thermal pack, permits it to warm and applies the device. Tissue warming occurs from direct contact of the attached thermal pack 61" to the underlying genital tissue. In all the thermal-producing embodiments, the heat generated by the device will result in increased clitoral blood flow and a further increase in sexual excitement above that provided by the vacuum alone.

The method of application of device 10, incorporating further structure to enhance clitoral stimulation (as shown and described above), to the user's body is includes several steps. The user compresses tip portion 16, thereby deforming the tip portion and reducing the air column within the entire interior vacuum chamber 18. The device 10 is then comfortably fitted over the clitoris, with body-contacting surface 29 of flange 26 placed in contact with the anterior vaginal vault tissue surrounding clitoris. Tip portion 16 is then released, permitting the device to expand to its original shape. The restorative deformation of tip portion 16 causes at least a partial vacuum to be provided within interior vacuum chamber 18. The vacuum environment serves to produce clitoral engorgement and increased sexual arousal while also serving to maintain device 10 in reliable sealed engagement with the user. The surrounding labial folds further secure device 10 to the clitoris and within the anterior vaginal vestibule. In this fashion, the labial folds both cover device 10 and prevent device migration. The user may now discreetly wear device 10 as she performs her daily tasks without further self-manipulation or embarrassment.

The deformation of tip portion 16 reduces the air volume within the entire interior vacuum chamber 18 and produces a partial vacuum. The force created by the differential pressure between the outside atmosphere pressure and the pressure within the interior vacuum chamber will attempt to force intermediate side walls 24 inward toward the center of the vacuum chamber. If intermediate side walls 24 were deformable (e.g., flat or concave inward), sufficient vacuum applied to interior vacuum chamber 18 would cause intermediate side walls 24 to collapse inward toward or into an abutting relationship. In this case, the normally distensible clitoris would be drawn into the compromised interior vacuum chamber 18 and compressed by the abutting intermediate side walls 24. Clitoral tissue could become entrapped and pinched by these abutting side walls 24. In the preferred embodiment, side walls 24 are shaped outwardly convex, like an arch, preventing inward movement of intermediate side walls 24 and thereby preventing clitoral entrapment and/or compression.

More precisely, the outwardly convex geometry of intermediate side walls 24 creates two functional chambers 18*a* and 18*b* which resemble a "bell." The lower vacuum chamber 18*b*, formed by the outwardly convex intermediate walls, serves as a substantially non-deformable, constant volume vacuum reservoir, while upper vacuum chamber 18*a*, formed by the tip portion, serves to create the vacuum due to its side wall deformation. In this fashion, lower vacuum chamber 18*b* evenly distributes suction to the clitoral tissue without compressing, obstructing or pinching clitoral tissue. Stated differently, the outwardly convex wall geometry allows the device to be of unitary construction and manufactured from a single, soft, deformable material. The lower vacuum chamber 18*b* may be composed of a soft, deformable material, yet be functionally non-deformable when vacuum is applied. Furthermore, the soft deformable material composing the non-deformable lower chamber and flange will minimize pressure necrosis to genital tissues when compared to rigid non-deformable materials, thus further preventing tissue damage.

As noted above, the user can alter the amount of vacuum in the interior vacuum chamber 18 by varying the degree of compression of the tip portion and thus the amount of air that is displaced. The greater the amount of manual compression to the tip portion, the greater the amount of displaced air and subsequent vacuum. In this manner, the user can advantageously regulate the amount of clitoral suction in order to generate a physiological response, rather than rely upon predetermined vacuum from an external vacuum source. The amount of vacuum necessary to stimulate female sexual arousal may vary depending upon the user and her pre-excitatory state but is preferable between about 40 mmHg and about 190 mmHg. Clinical testing has demonstrated that this negative pressure range maximizes clitoral blood flow without causing discomfort, bleeding and tissue injury.

To achieve an optimal response, clinical testing has shown that the device should initially be utilized for a period of time to condition the genital tissues also known as a "conditioning period." Users should apply the device for a specified period of time; up to as long as several weeks; preferably one to four weeks. The device should be applied on a daily basis for a predetermined period; for as long as approximately thirty minutes. This "conditioning period" is important to stimulate blood flow to the genital tissues. Once the "conditioning period" is complete, and additional blood flow has been stimulated, the user then applies the device only before vaginal sex. In the preferred method, the user applies the device approximately thirty minutes before engaging in vaginal sex to acutely increase blood flow and enhance sexual arousal. The user removes the device before vaginal sex.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Furthermore, all of the supplemental structures may be used in combination with the vacuum producing device to increase the overall efficiency of the device and enhance stimulation of the user. Accordingly, the foregoing description and drawings are by way of example only.

What is claimed is:

1. A female stimulation device comprising: a device body for producing a vacuum consisting of a tip portion, a flange, and an intermediate side wall portion extending from said tip portion to said flange; and means for enhancing clitoral blood flow when applied to a user wherein said means for enhancing clitoral blood flow comprises at least one of a mechanical, vibratory, or heating component that is within or outside one of said tip portion, said flange, or said intermediate side wall portion while also being in contact with one of said tip portion, said flange, or said intermediate side wall portion.

2. The device as claimed in claim 1, wherein said flange is sized and shaped to encompass the female clitoris.

3. The device as claimed in claim 2, wherein said tip portion is deformable and defines a vacuum producing upper chamber.

4. The device as claimed in claim 3, wherein said intermediate side wall portion is outwardly convex and defines a vacuum reservoir lower chamber.

5. The device as claimed in claim 4, wherein said lower chamber portion is non-deformable.

6. The device as claimed in claim 5, wherein said device body is constructed from a resilient material.

7. The device as claimed in claim 3, wherein said vacuum producing upper chamber produces vacuum to promote clitoral blood flow without causing injury to underlying tissue.

8. The device as claimed in claim 7, wherein said vacuum producing upper chamber produces a vacuum of between about 40 and about 190 mmHg.

9. The device as claimed in claim 8, wherein said means for enhancing clitoral blood flow is positioned within at least one of the vacuum producing upper chamber and the vacuum reservoir lower chamber.

10. The device as claimed in claim 9, wherein said means for enhancing clitoral blood flow comprises a plurality of flexible attachments that extend into the vacuum reservoir lower chamber.

11. The device as claimed in claim 8, wherein said means for enhancing clitoral blood flow comprises a channel positioned between the tip portion and the intermediate side wall portion and at least one roller element positioned within the channel.

12. The device as claimed in claim 8, wherein said means for enhancing clitoral blood flow comprises motor positioned on one of an end wall of the tip portion and the intermediate side wall portion.

13. The device as claimed in claim 8, wherein said means for enhancing clitoral blood flow comprises a heat-producing compound positioned on a body-contacting surface of the device.

14. The device as claimed in claim 1, wherein a material selected from the group consisting of an adhesive, a lubricant, a vasoactive substance, and mixtures thereof is disposed on a portion of said flange.

15. The device as claimed in claim 14, wherein said material has a thickness of less than about 3 mm.

16. The device as claimed in claim 15, wherein a coating is placed on top of said material.

17. The device as claimed in claim 1, wherein a material selected from the group consisting of a lubricant, a vasoactive substance, and mixtures thereof is disposed on an inside wall of said tip portion.

18. A method for facilitating female stimulation for producing a vacuum consisting of providing a device comprising a tip portion, a flange, an intermediate side wall portion extending outwardly from said tip portion to said flange, and means for enhancing clitoral blood flow when applied to a user, wherein said flange is sized and shaped to encompass the female clitoris, said intermediate side wall portion is outwardly convex and defines a vacuum reservoir lower chamber, said tip portion is deformable and defines a vacuum producing upper chamber, and said means for enhancing clitoral blood flow comprises at least one of a mechanical, vibratory, or heating component that is within or outside one of said tip portion, said flange, or said intermediate side wall portion while also being in contact with one of said tip portion, said flange, said intermediate side wall portion; and providing instruction to apply said device to promote clitoral blood flow without causing injury to underlying tissue.

19. The method of claim 18, further comprising providing a material selected from the group consisting of an adhesive; a lubricant vasoactive substance, and mixtures thereof.

20. The method of claim 19, further comprising providing instructions to apply said material on a portion of said flange prior to applying said device.

21. The method of claim 18, wherein said means for enhancing clitoral blood flow is positioned within at least one of the vacuum producing upper chamber and the vacuum reservoir lower chamber.

22. The method of claim 21, wherein said means for enhancing clitoral blood flow comprises a plurality of flexible attachments that extend into the vacuum reservoir lower chamber.

23. The method of claim 18, wherein said means for enhancing clitoral blood flow comprises a channel positioned between the tip portion and the intermediate side wall portion and at least one roller element positioned within the channel.

24. The method of claim 18, wherein said means for enhancing clitoral blood flow comprises a motor positioned on one of un end wall of the tip portion and the intermediate side wall portion.

25. The method of claim 18, wherein said means for enhancing clitoral blood flow comprises a heat-producing compound positioned on a body-contacting surface of the device.

26. A method for enhancing female stimulation, for producing a vacuum consisting of the steps of: providing a female stimulation device comprising a tip portion, a flange, an intermediate side wall portion extending from said tip portion to said flange and defining an interior vacuum chamber, and means for enhancing clitoral blood flow when applied to a user, wherein said means for enhancing clitoral blood flow comprises at least one of a mechanical, vibratory, or heating component that is within or outside one of said tip portion, said flange, or said intermediate side wall portion while also being in contact with one of said tip portion, said flange, or said intermediate side wall portion, and compressing said tip portion to reduce an air column formed within said interior vacuum chamber; placing said device over the female clitoris such that said flange is placed into contact with anterior vaginal vault tissue and said means for enhancing clitoral blood flow is in operative contact with said anterior vaginal vault tissue; releasing said tip portion to produce vacuum in said interior vacuum chamber, wherein said vacuum causes clitoral engorgement and maintains engagement of said device with said anterior vaginal vault tissue; and removing said device after a predetermined period of time.

27. The method of claim 26, further comprising: repeating said steps periodically to condition genital tissues.

28. The method of claim 26, further comprising: applying a material selected from the group consisting of an adhesive, a lubricant a vasoactive substance, and mixtures thereof on a portion of said flange prior to placing said device into contact with said anterior vaginal vault tissue.

* * * * *